United States Patent
Sakamoto et al.

[11] Patent Number: 6,063,035
[45] Date of Patent: May 16, 2000

[54] COUPLING ADAPTOR FOR ENDOSCOPICALLY INSERTING ULTRASOUND PROBE

[75] Inventors: Toshio Sakamoto; Toshizumi Tanaka; Hiromu Itoi; Masatoshi Yoshihara, all of Omiya, Japan

[73] Assignee: Fuji Photo Optical Co., Ltd., Omiya, Japan

[21] Appl. No.: 09/120,882

[22] Filed: Jul. 23, 1998

[30] Foreign Application Priority Data

| Jul. 24, 1997 | [JP] | Japan | 9-212715 |
| Aug. 22, 1997 | [JP] | Japan | 9-240293 |
| Aug. 22, 1997 | [JP] | Japan | 9-240294 |
| Aug. 28, 1997 | [JP] | Japan | 9-245909 |

[51] Int. Cl.$^7$ .................................................. A61B 8/00
[52] U.S. Cl. ............................................................. 600/462
[58] Field of Search .................................. 600/459, 461, 600/462, 464, 467, 466, 104

[56] References Cited

U.S. PATENT DOCUMENTS

| 5,417,216 | 5/1995 | Tanaka | 600/462 |
| 5,464,016 | 11/1995 | Nicholas et al. | 600/464 |
| 5,827,175 | 10/1998 | Tanaka | 600/104 |

*Primary Examiner*—Marvin M. Lateef
*Assistant Examiner*—Maulin Patel
*Attorney, Agent, or Firm*—Oblon, Spivak, McClelland, Maier & Neustadt, P.C.

[57] ABSTRACT

A coupling adaptor for electrically and rotationally coupling a tail end connector of an endoscopically inserting ultrasound probe with a connector portion of a separate probe control unit. The coupling adaptor is intended for use with an endoscopically inserting ultrasound probe having a bulky ultrasound scanner assembly at the nose end of a flexible cord, and a thin and narrow tail end connector at the proximal end of the flexible cord for passage through a biopsy channel of an endoscope. The coupling adaptor is provided with, within a stationary housing, a pair of rotationally interconnected front and rear rotary members to be disconnectibly coupled with the tail end connector of the ultrasound probe and a rotational drive means on the probe control unit, respectively. The front and rear rotary members of the coupling adaptor internally carry electrical connection means to establish electrical connections between the ultrasound probe and the probe control unit when coupled therewith to transmit rotation from the rotational drive means on the probe control unit to an ultrasound transducer element on the ultrasound scanner assembly provided at the distal end of the flexible cord of the ultrasound probe.

15 Claims, 15 Drawing Sheets

COUPLING ADAPTOR FOR ENDOSCOPICALLY INSERTING ULTRASOUND PROBE

FIELD OF THE ART

This invention relates generally to an ultrasound examination system employing an endoscopically inserting ultrasound probe to be introduced into a body cavity through a biopsy channel within an endoscopic insertion instrument, and more particularly to a coupling adaptor for rotationally and electrically coupling an endoscopically inserting ultrasound probe with a separate probe control unit.

PRIOR ART

Regarding ultrasound examination systems for acquiring information on intracorporeal tissues, it has been known to introduce an endoscopically inserting ultrasound probe into a body cavity through an endoscopic instrument channel or a biopsy channel which is provided within an endoscopic insertion instrument. An ultrasound examination system of this sort is largely constituted by an ultrasound probe, a probe controller and an ultrasound image observation terminal. For making ultrasound scans, the ultrasound probe is provided with an ultrasound scanner head at the tip end of a flexible cord. The ultrasound scanner head has an ultrasound transducer element housed in an end cap fixedly attached to the tip end of the flexible cord. The probe controller serves to control the operations of the ultrasound transducer element, and the ultrasound image observation terminal includes an ultrasound driver which drives the ultrasound transducer element for transmission of ultrasound pulses, along with a signal processor for processing received ultrasound echo signals into ultrasound images to be displayed on a monitor screen.

For placement in an endoscopic biopsy channel, a major part of the ultrasound probe is constituted by a flexible cord of a smaller diameter as compared with the inside diameter of the endoscopic biopsy channel. In an ultrasound scanning operation, while transmitting ultrasound pulse signals toward an intracorporeal portion of interest at predetermined intervals, return echoes are received and converted into electrical signals through the ultrasound transducer element to acquire information of intracorporeal tissues over a predetermined range. The ultrasound transducer element is scanned in a linear direction in a linear ultrasound scanning operation and in a radial or rotational direction in a radial ultrasound scanning operation. In the case of a linear scan, the flexible cord of the ultrasound probe is pushed back and forth in a linear direction. In the case of a radial ultrasound scan, the ultrasound transducer element needs to be put in rotation by the use of a motor or other rotational drive means, which however is too bulky to provide at the distal end of the ultrasound probe. Therefore, it is the usual practice to provide on the ultrasound probe a rotation transmission means, which permits to remote-control the rotation of the ultrasound transducer element, in cooperation with a rotational drive means and rotational angle detection means which are provided on the part of the probe controller of the ultrasound examination system. For this purpose, the probe controller may be provided separately from an ultrasound image observation terminal, or, if desired, may be assembled into an ultrasound image observation terminal as an integral part thereof.

As the rotation transmission means, it has been the general practice to provide on the ultrasound probe a flexible shaft which is connected to the ultrasound transducer element at its fore end. The flexible shaft of this sort is usually in the form of a hollow coil tube consisting of layers of tightly wound coils and internally providing a passage for a cable to be connected to the ultrasound transducer element. The flexible shaft is fitted in a flexible sheathing tube and rotatable therein to transmit its rotation to the distal end of the probe to rotate the ultrasound transducer element. The end cap which accommodates the ultrasound transducer element is formed of a material with excellent acoustic characteristics, and at least the inner space of the end cap is filled with an ultrasound transmitting medium.

The ultrasound probe is provided with a connector at its proximal end for disconnectibly coupling same with the ultrasound controller. The connector is largely constituted by a fixed part which is connected to the sheathing tube, and a rotating part which is connected to the flexible shaft through an internal space of the fixed part. The probe controller is provided with a rotational shaft to be disconnectibly coupled with the rotating part of the connector, along with a retaining member which is located around the rotational shaft for fixedly holding the fixed part of the connector. A cable which is passed through the flexible shaft is electrically connected to the probe controller through electrode members provided in the rotating part. Accordingly, upon coupling the rotating part of the connector with the rotational shaft on the part of the probe controller, the electrodes of the rotating part are electrically connected with corresponding electrodes on the side of the rotational shaft.

When the probe controller is operated to actuate the rotational drive of the rotational shaft, its rotation is transmitted to the flexible shaft through the rotating part of the connector, while the sheathing tube which is fitted on the flexible shaft is retained in a fixed state without rotating together with the flexible shaft. As will be understood from the foregoing description, in addition to the function of rotationally driving the flexible shaft, the probe controller has functions as a signal relay means.

Since the outside diameter of the ultrasound probe is restricted by the inside diameter of an endoscopic biopsy channel on the endoscope, the ultrasound transducer element can only have an active surface of a limited size for transmission and reception of ultrasound signals. An ultrasound transducer element with a smaller active surface is higher in vibrational frequency and lower is power. Therefore, a small-size transducer element is incapable of sending ultrasound pulses to deepest positions in the patient's body, and suffers from a low S/N ratio since return echoes are weak and susceptible to influences of external noises. In this connection, in the case of a front loading type ultrasound probe which is designed to be placed in an endoscopic biopsy channel from an inverse direction, that is to say, from the fore distal end of an endoscopic insertion instrument, it is possible to employ a bulky ultrasound scanner assembly with a large ultrasound transducer element of large power and low frequency because in this case there is no necessity for passing the ultrasound scanner assembly through the narrow endoscopic biopsy channel in a preparatory stage prior to introduction into a body cavity.

On the other hand, the connector at the tail end of an ultrasound probe is free from the dimensional restrictions as imposed by the inside diameter of an endoscopic biopsy channel in case the ultrasound probe is of the type which is designed to be placed in an endoscopic biopsy channel from its nose end which supports an ultrasound scanner assembly. It follows that in that case the tail end connector can be formed in a larger diameter than an endoscopic biopsy channel if necessary for the purpose of increasing the strength of the connector. However, in the case of an ultrasound probe which is designed to be placed in an endoscopic biopsy channel from its tail end through an opening at the fore end of an endoscopic insertion instrument, it is a must for the tail end connector and flexible cord to be thinner than the inside diameter of the endoscopic biopsy channel. Therefore, in practical use, the tail end connector is found too fragile and easily damaged when hit against other objects. Besides, a thin tail end connector requires very delicate handling since it can be damaged even when coupled with or uncoupled from a probe controller which is retained in a fixed state.

SUMMARY OF THE INVENTION

In view of the foregoing situations, it is an object of the present invention to provide protection for a thin tail end connector of an endoscopically inserting ultrasound probe, which needs to be placed in an endoscopic biopsy channel inversely from its tail end due to use of a bulky large-size ultrasound transducer element on an ultrasound scanner assembly at the nose end of the probe, permitting to couple and uncouple the tail end connector with and from a probe controller in a facilitated manner and in a protected state.

It is another object of the present invention to provide a rotational and electrical coupling mechanism which facilitates coupling and uncoupling of a thin tail end connector of an endoscopically inserting ultrasound probe with and from a separate probe control unit.

More specifically, in accordance with the present invention, there is provided a coupling adaptor for use with an ultrasound examination system employing an endoscopically inserting ultrasound probe to be introduced into a body cavity through a biopsy channel provided in an endoscopic insertion instrument. Especially, the coupling adaptor according to the present invention is intended for use with an ultrasound probe having a bulky ultrasound scanner assembly at the nose end of an elongated flexible cord which contains a flexible rotation transmission means along with an electrical signal cable to and from an ultrasound transducer element on the ultrasound scanner assembly, and a thin and narrow tail end connector provided at the tail end of the flexible cord for electrically and rotationally coupling the ultrasound probe with a rotational drive and electrical contact portions on a separate probe control unit, both of the flexible cord and the tail end connector having an outside diameter smaller than the inside diameter of the endoscopic biopsy channel for passage therethrough. The coupling adaptor is disconnectibly connectible with the tail end connector of the ultrasound probe for electrically and rotationally coupling same with the probe control unit in a protected state, the coupling adaptor is provided with, within a stationary housing, a pair of rotationally interconnected front and rear rotary members to be disconnectibly coupled with the tail end connector and the rotational drive means on said probe control unit, respectively, the front and rear rotary members of the coupling adaptor internally carrying electrical connection means to establish electrical connections between the ultrasound probe and the probe control unit when coupled therewith to transmit rotation from the rotational drive means on the probe control unit to the ultrasound transducer element on the ultrasound scanner assembly at the distal end of the ultrasound probe.

The above and other objects, features and advantages of the present invention will become apparent from the following particular description of the invention, taken in conjunction with the accompanying drawings which show by way of example some preferred embodiments of the invention.

DESCRIPTION OF PREFERRED EMBODIMENTS

Figure 1:
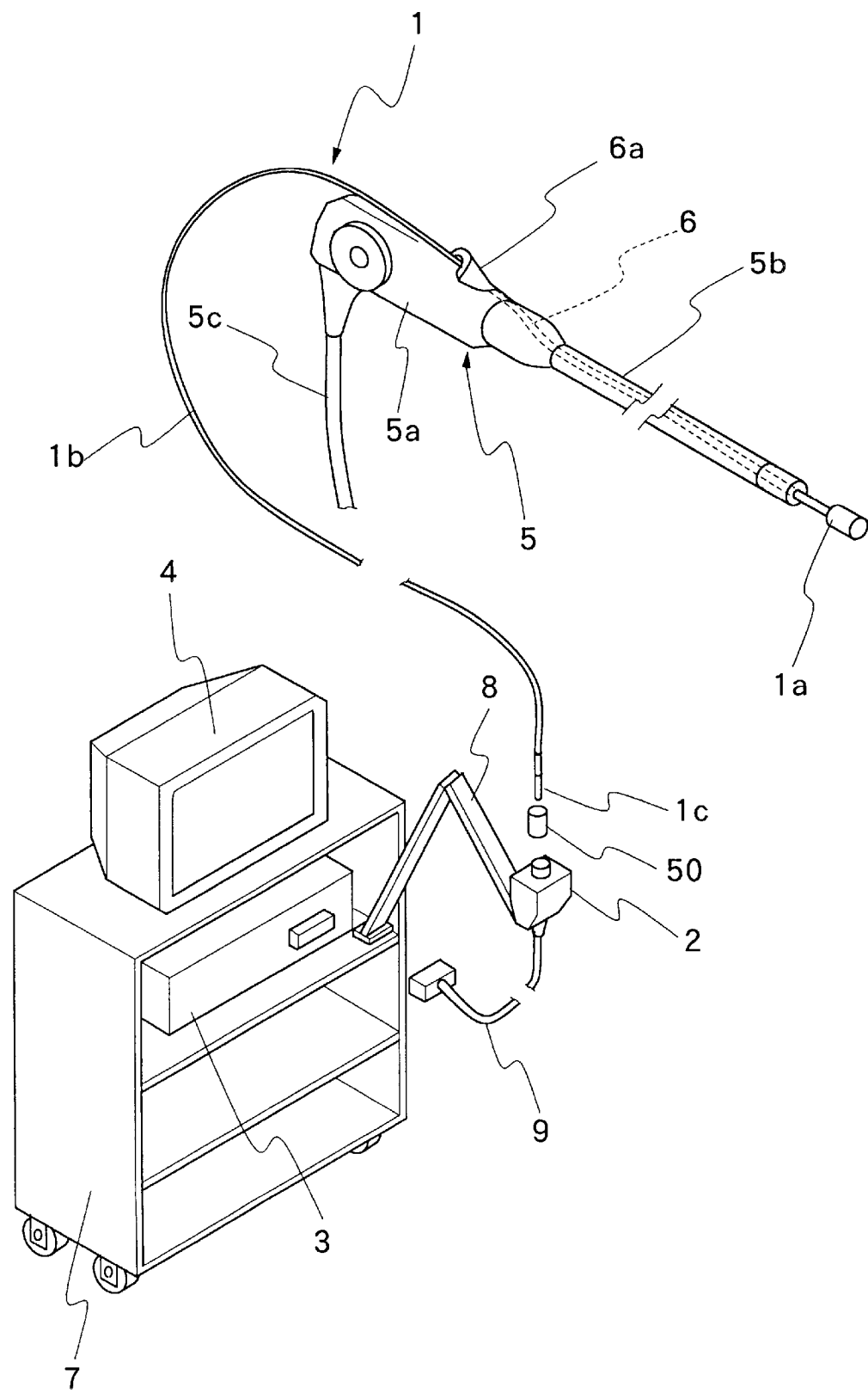
FIG. 1 is a schematic illustration of the general layout of an ultrasound examination system incorporating a probe coupling adaptor according to the present invention.

Hereafter, the present invention is described more particularly by way of its preferred embodiments shown in the drawings. Schematically shown in FIG. 1 is the general layout of an ultrasound examination system incorporating an ultrasound probe coupling adaptor according to the present invention. The ultrasound examination system is largely composed of an ultrasound probe 1, a probe control unit 2 and an ultrasound image observation terminal 3 with a monitor screen 4. The ultrasound probe 1 is of the type which is introduced into a body cavity by way of an endoscope 5, more specifically, by way of a biopsy channel 6 which is provided axially and internally of an endoscopic insertion instrument 5b and accessible through an entrance housing 6a, which is provided on a manipulating head grip 5a of the endoscope 5. Led out from the manipulating head grip 5a of the endoscope 5 is a universal cable 5c to be connected to a light source and an ultrasound signal processor which are not shown in the drawings. In this instance, the ultrasound image observation terminal 3 with a monitor screen 4 is mounted on a rack 7, and the probe control unit 2 is mounted on a fore end portion of a foldable support arm 8 which is in turn connected to the rack 7 in such a way as to permit directional adjustments. A cable 9 which is led out from the probe control unit 2 is disconnectibly connected to the ultrasound image observation terminal 3.

Figure 2:
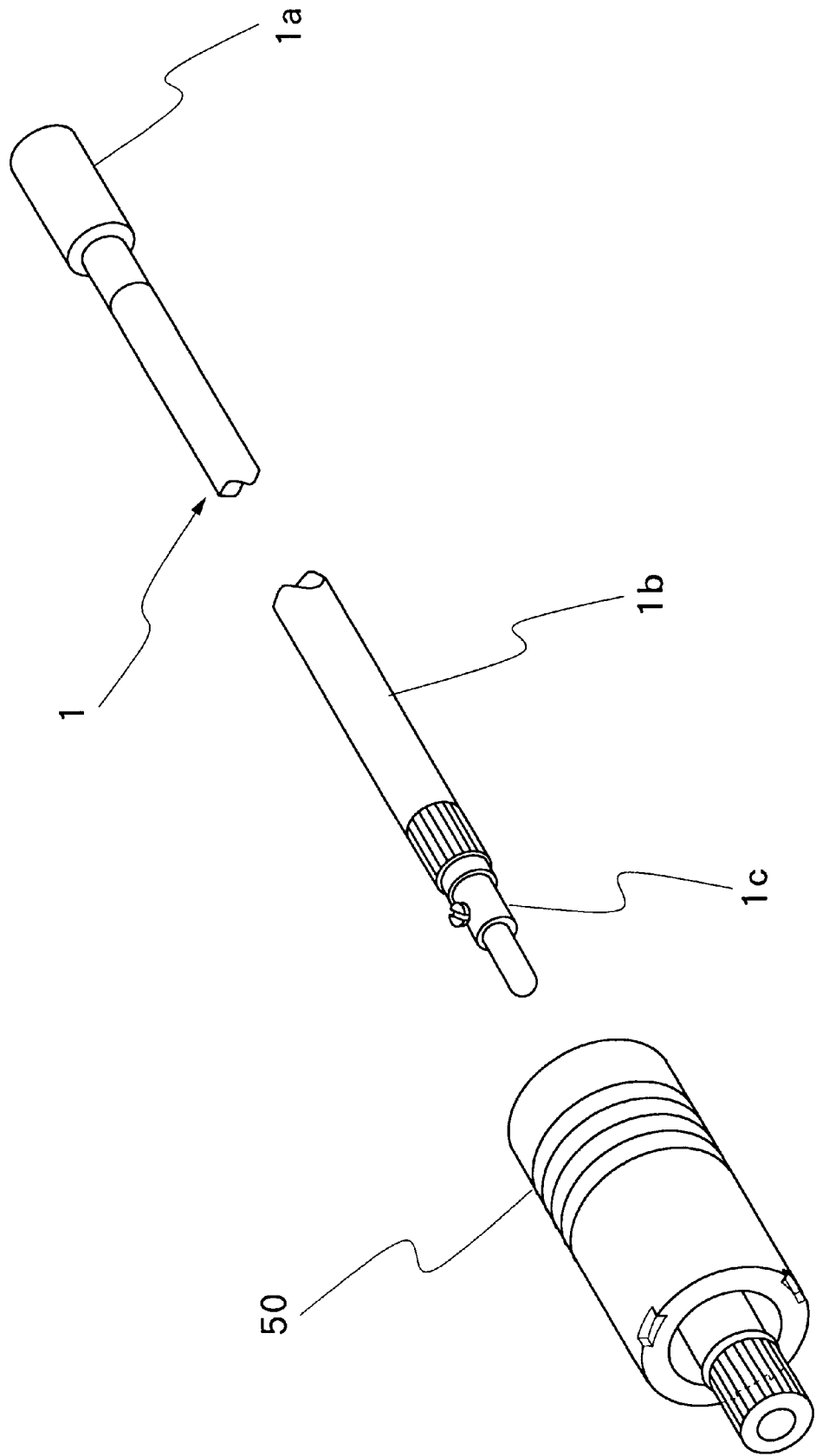
FIG. 2 is a fragmentary schematic view of an ultrasound probe and a coupling adaptor.
Figure 3:
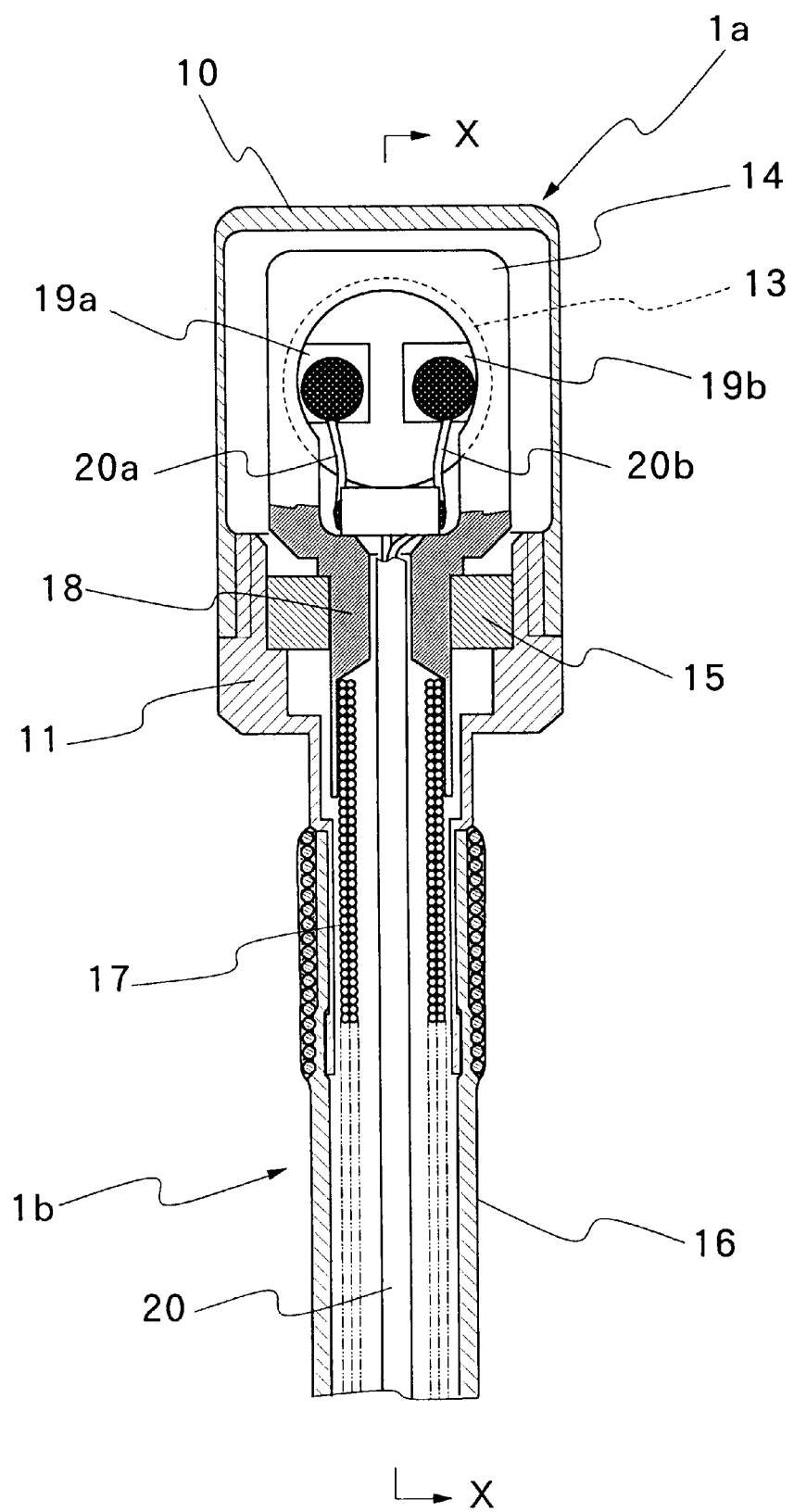
FIG. 3 is a fragmentary longitudinal section of a nose end portion of the ultrasound probe.
Figure 4:
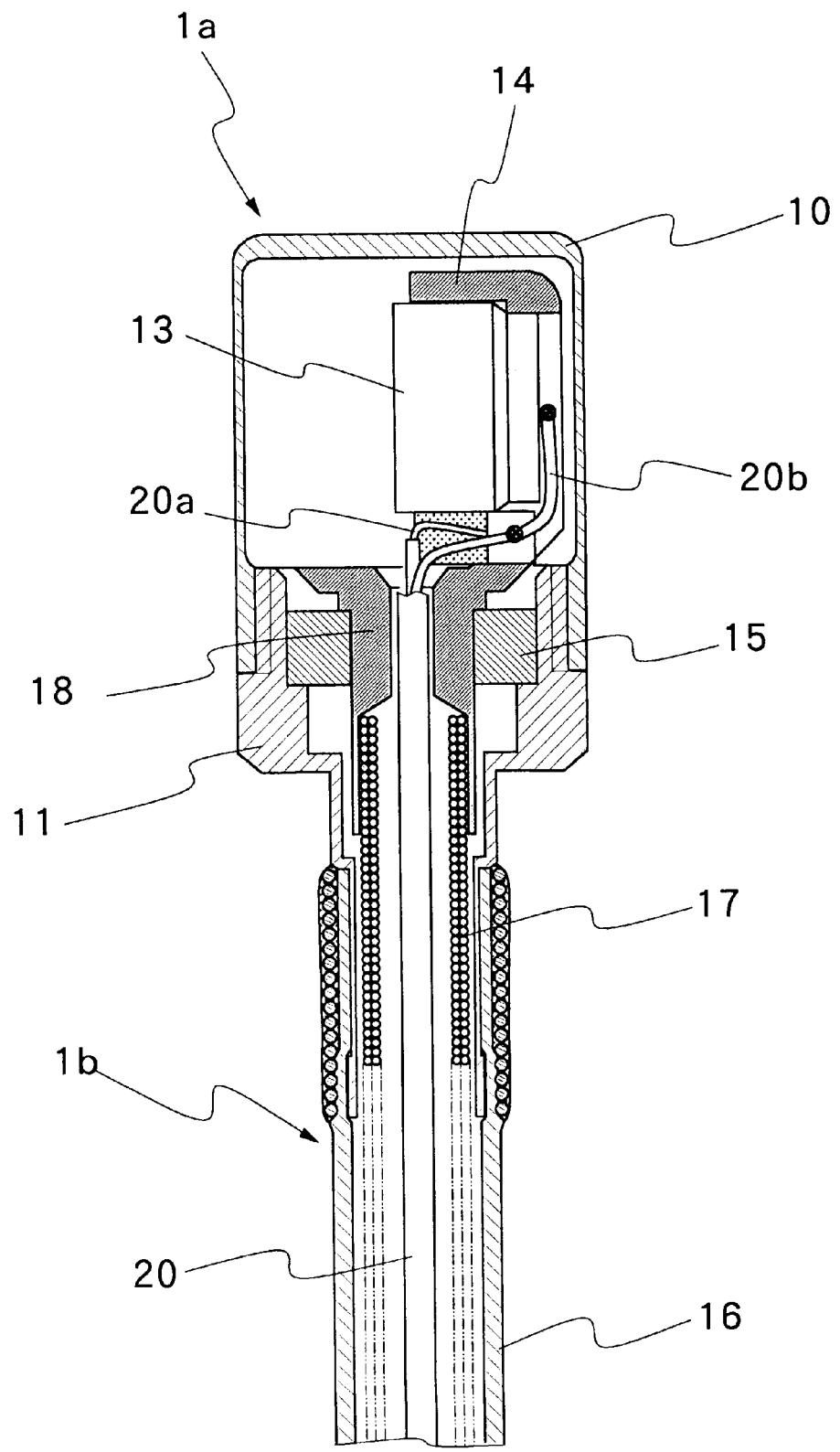
FIG. 4 is a longitudinal sectional view taken on line X—X of FIG. 3.

The ultrasound probe 1 as a whole is constructed as shown in FIG. 2. More specifically, as seen in FIG. 2, the ultrasound probe 1 is largely constituted by an ultrasound scanner assembly 1a, a flexible cord 1b and a tail end connector 1c. As shown particularly in FIGS. 3 and 4, the ultrasound scanner assembly 1a is provided with an end cap 10 which is connected to a connecting member 11. The ultrasound transducer element 13 is accommodated in the end cap 10, and mounted on a rotary member 14 which is rotatably supported within the end cap 10 through a bearing 15 to scan the ultrasound transducer element 13 in the radial direction. For accommodating a large-size ultrasound transducer element with a broad active surface area which can transmit strong ultrasound signals, the end cap 10 is of a bulky size having an outside diameter as larger than the inside diameter of the endoscopic biopsy channel 6 as possible within a range which would not obstruct the view field of endoscopic observation.

The flexible cord 1b is constituted by a flexible outer tube 16 of soft synthetic resin material or the like, and a flexible rotation transmission shaft 17 which is fitted in the outer tube 16. Fixedly connected to the fore distal end of the outer tube 16 is the connecting member 11 which is in turn fixedly connected to the end cap 10. The flexible transmission shaft 17 is constituted, for example, by tightly wound coils, preferably, by double layers of tightly wound coils of metal wires for transmitting rotations accurately in a reliable manner. The fore distal end of the flexible shaft 17 is securely fixed to a hollow neck member 18 which is integrally connected to the rotary member 14. The ultrasound transducer element 13 is provided with a pair of electrodes 19a and 19b to connect signal lines 20a and 20b of a coaxial cable 20 which is passed through the neck member 18 and extended as far ss the tail end connector 1c of the probe 1 through the internal space of the flexible shaft 17.

Figure 5:
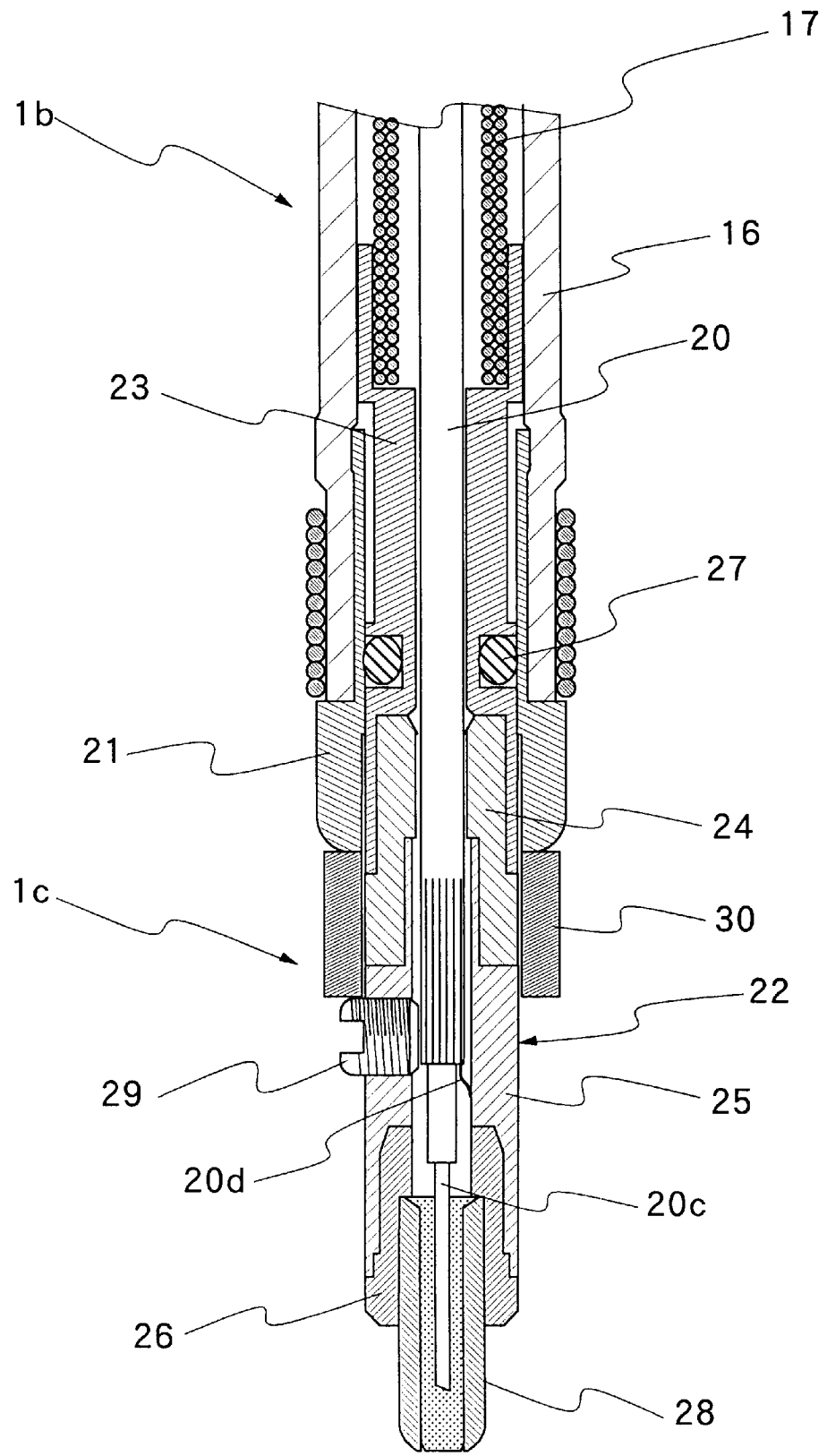
FIG. 5 is a longitudinal sectional view of a tail end portion of the ultrasound probe.

Shown on an enlarged scale in FIG. 5 is the probe construction where the proximal end of the flexible cord 1b is terminated with the tail end connector 1c. More specifically, the proximal end of the outer tube 16 is fixedly fitted on a tubular retainer shell 21 of metal. The proximal end of the flexible shaft 17 is connected to a rotational ring assembly 22 including an electrode ring. In this instance, the ring assembly 22 is composed of four rotary members or rings 23 to 26 which are successively threaded one in another in the axial direction. The first rotary ring 23 which is directly connected to the flexible shaft 17 is formed of a rigid metallic material with a sufficient degree of shape retainability and received in the retainer shell 21, which is similarly formed of a rigid metallic material, for sliding rotational movements therein. A seal member 27 is fitted on the first rotary ring 23 to seal off the clearance between the first rotary ring 23 and the retainer shell 21 air- and liquid-tight. Connected to the first rotary ring 23 is a second rotary ring 24 which is formed of an electrically insulating material such as a synthetic resin material or the like. A third rotary ring 25 which is connected to the second rotary ring 24 is formed of a metal or other conducting material, while a fourth rotary member 26 which is connected to the third rotary ring is formed of an electrically insulating material.

In this case, for the purpose of ensuring the sealing capacity by the seal member 27, the first rotary ring 23 is formed of a metal or metallic material. The third rotary ring 25 is formed of a metal because it is required to function as an electrode to be connected to the ultrasound transducer element 13. Accordingly, the second and fourth rotary members 24 and 26 of electrically insulating material are located on the front and rear sides of the third rotary ring 25. The coaxial cable 20 is passed internally through the ring assembly 22, with its core wire 20c connected to a pin 28, which is fitted in the fourth rotary member 26, and its shield wire 20d connected to the third rotary ring 25.

Further, a rotation transmission pin 29 is securely planted in the third rotary ring 25. As described hereinlater, the transmission pin 29 functions to transmit rotation to the ring assembly 22, and is arranged in such a way as to project radially outward from the outer periphery of the third rotary ring 25 by a predetermined length. A spacer ring 30 is fitted on the outer periphery of the ring assembly 22 between the rotation transmission pin 29 and the retainer shell 21. This spacer ring 30 is abutted against the front side of the rotation transmission pin 29 and rear end face of the retainer shell 21, thereby to retain the ring assembly 22, the flexible shaft 17 which is connected to the ring assembly 22, the flexible tube 16 and the retainer shell 21 in an inseparably assembled state. The spacer ring 30 is formed of an electrically insulating synthetic resin material or the like with suitable slipperiness. Thus, by the spacer ring 30, the retainer shell 21 is electrically insulated from the third rotary ring 25 and the rotation transmission pin 29 which are both formed of a metallic material.

Figure 6:
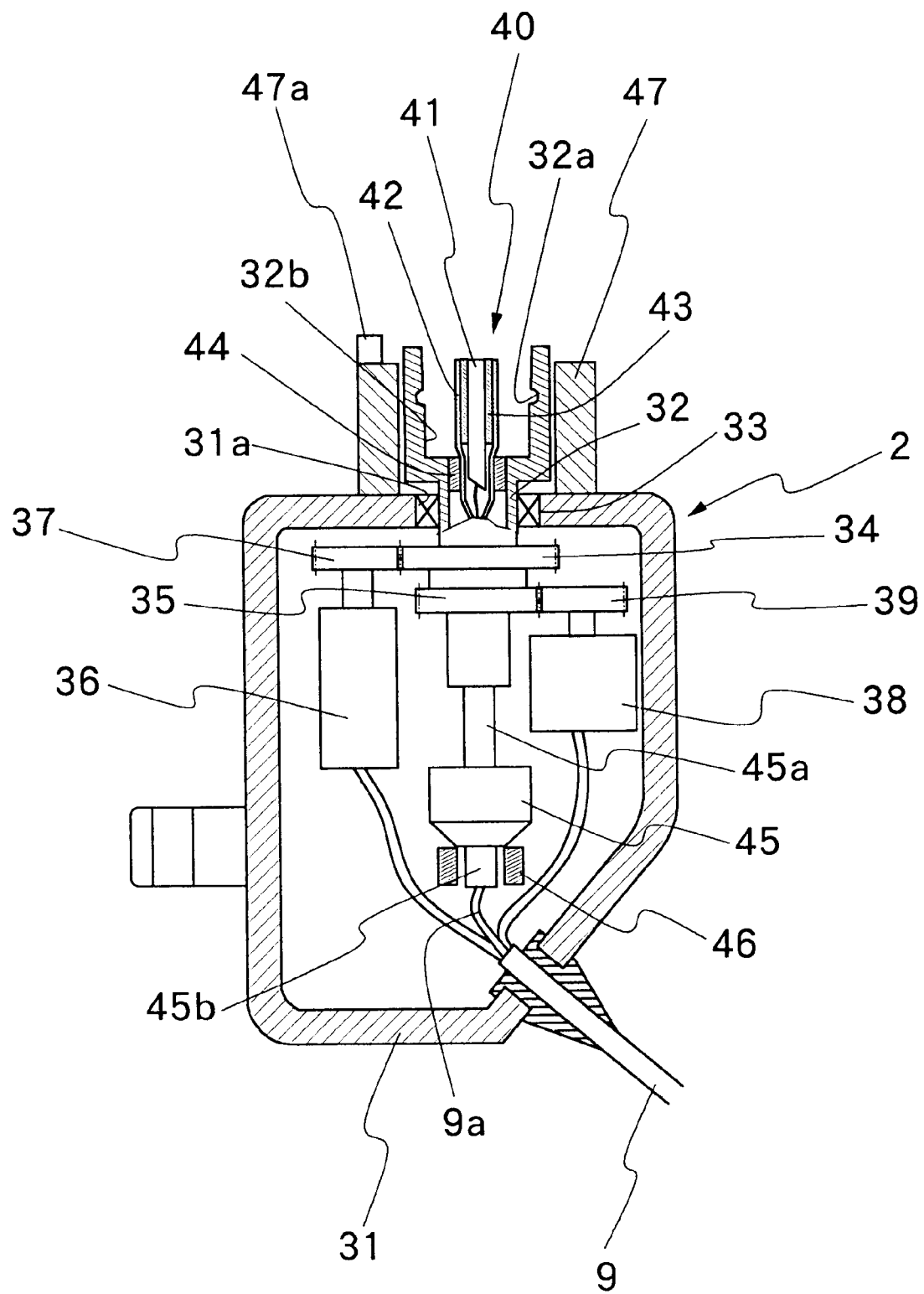
FIG. 6 is a schematic sectional view of a probe control unit.

Referring now to FIG. 6, the probe control unit 21 is provided with a casing 31 of an electrically insulating synthetic resin material or the like, in which a rotational shaft 32 is rotatably mounted through a bearing 33 to extend toward an opening 31a which is provided on the front side of the casing 31. Mounted on the rotational shaft 32 are a pair of gears 34 and 35. One gear 34 is meshed with a drive gear 37 which is mounted on an output shaft of an electric motor 36, while the other gear 35 is meshed with a follower gear 39 which is mounted on an input shaft of an encoder 38. Provided internally of the rotational shaft 32 is an electrode member 40 which is constituted by an inner pipe 41 and an outer pipe 42. These inner and outer pipes 41 and 42 are formed of an electrically conducting material and insulated from each other by an interposed insulating pipe 43. In addition, the outer pipe 42 is fitted in an insulating ring 44 which is fixedly fitted in the rotational shaft 32. Thus, by an adaptor 50 which will be described hereinlater, the core and shield wires 20c and 20d of the coaxial cable 20 are electrically connected to the inner and outer pipes 41 and 42, respectively.

One end of the rotational shaft 32 is disposed in the opening 31a on the front side of the casing 31 as mentioned hereinbefore, while the other end of the rotational shaft 32 is connected to a rotary member 45a on the rotating side of the rotary connector 45 which is provided within the casing 31. A cable 9a of the cable assembly 9 to and from the ultrasound image observation terminal is connected to a fixed member 45b on the stationary side of the rotary connector 45. The fixed member 45b of the rotary connector 45 is fitted in a rotation blocking member 46 thereby to block its rotational movements and at the same time to restrict its radial fluttering movements. A cylindrical connection housing 47 is erected around and on the outer side of the opening 31a in such a way as to circumvent the rotational shaft 32.

Figure 7:
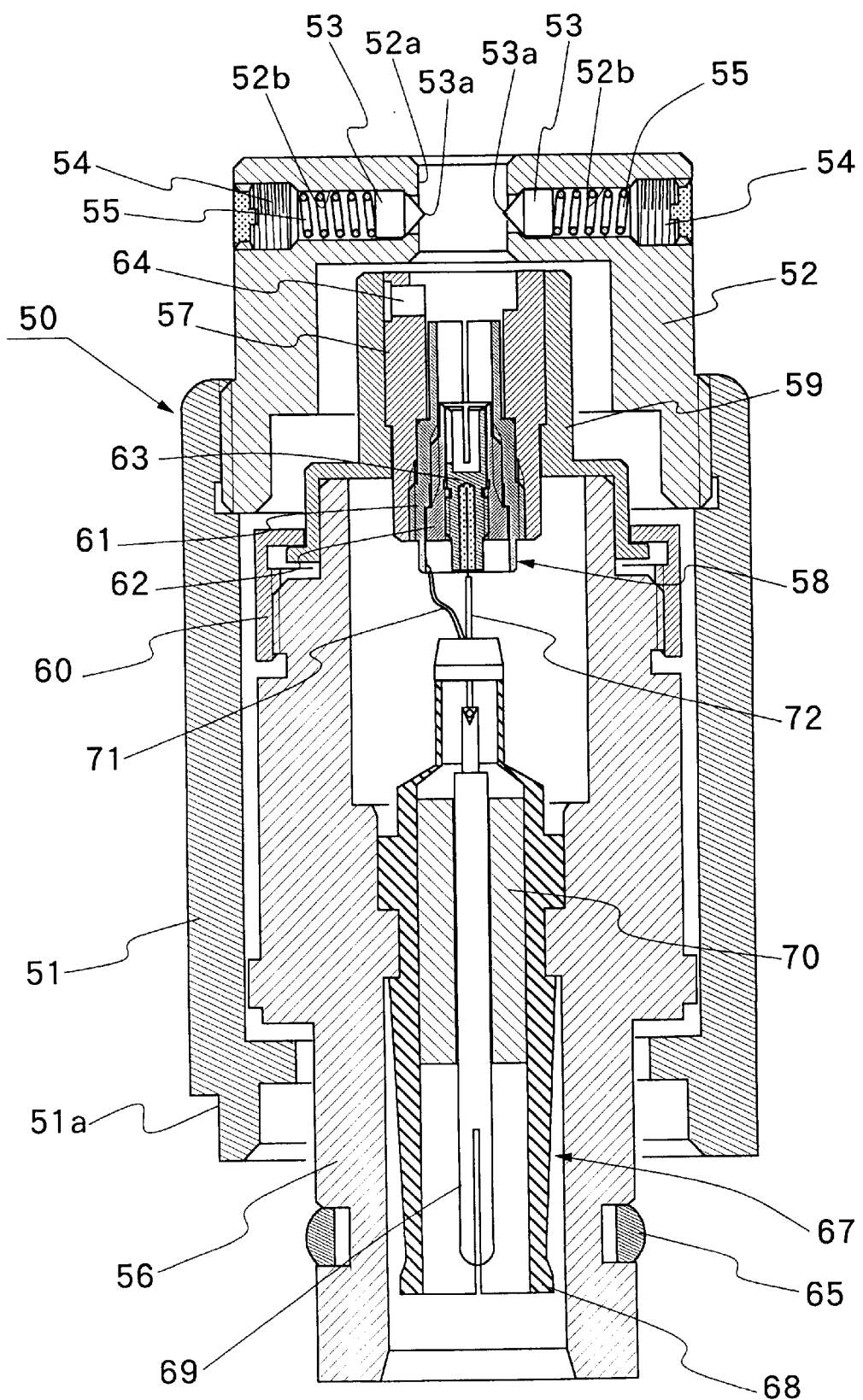
FIG. 7 is a schematic sectional view of a coupling adaptor in a first embodiment of the present invention.

The tail end connector 1c of the ultrasound probe 1 is coupled with the above-described probe control unit 2 not directly but through a coupling adaptor 50 as described below. The coupling adaptor 50 is provided with a first or front coupling mechanism at one end to be connected to the tail end connector 1c of the probe and a second or rear coupling mechanism at the other end to be connected to the probe control unit 2. More specifically, as shown particularly in FIG. 7, the coupling adaptor 50 is provided with stationary members including an outer housing 51 of substantially cylindrical shape and a retainer cap 52 which is threaded into one end of the outer housing 51. These stationary members of the adaptor are securely fixable relative to the casing 31 of the probe control unit 2. To this end, the outer housing 51 is provided with a stopper groove 51a which is engaged with a stopper projection 47a on the part of the connection housing 47 of the probe control unit 2 to block relative rotations of the fixed member of the adaptor 50 when connected to the latter. Further, the retainer cap 52 of the adaptor 50 is provided with an axial hole 52a to receive the retainer shell 21 of the tail end connector 1c of the probe 1. The retainer cap 52 is provided with a plural number of radial through holes 52b in its front end wall across the axial hole 52a to receive fixing screws 53, which are retractably protrudable into the axial hole 52a. More specifically, the fixing screws 53 are urged into the protruding positions by biasing springs 55 which are charged between the respective fixing screws 53 and spring seats 54. The fixing screws 53 are pointed at the respective inner ends for engagement in axial grooves (not shown) which are provided on the outer peripheral surface of the retainer shell 21 of the tail end connector 1c as rotation blocking grooves. When tail end connector 1c is inserted into the axial hole 52a of the retainer cap 52 up to the retainer shell 21, the pointed ends of the fixing screws 53 are engaged with the stopper grooves to block rotations of the retainer shell 21 and the outer tube 16 of the probe 1 during radial ultrasound scans when the ultrasound transducer element 13 is rotated through the flexible shaft 17.

The coupling adaptor 50 is further provided with rotary members internally of its stationary members including the housing 51 and the retainer cap 52. Major rotary members are rear and front rotary members 56 and 57 of generally hollow cylindrical shapes. A socket assembly 58 is threaded into the front rotary member 57 to receive the tail end connector 1c of the ultrasound probe 1 therein. The front rotary member 57 itself is threaded into a retainer ring 59 which is fixedly connected to the rear rotary member 56 by a box nut 60. A first tubular electrode pin 61 of the socket assembly is threaded into the front rotary member 57, which is formed of an electrically insulating material. A tubular insulating member 62 is threaded into the first tubular electrode pin 61, and a second tubular electrode pin 63 is fitted in this tubular insulating member 62. The first and second electrode pins 61 and 63 are in the form of axially split pins with spring characteristics. Further, a radial drive pin 64 is provided on the front rotary member 57, the drive pin 64 being abutted against the rotation transmission pin 29 on the part of the tail end connector 1c of the ultrasound probe 1 when the latter is connected to the coupling adaptor 50. By abutting engagement of the drive pin 64 with the rotation transmission pin 29, rotation is transmitted from the rotary members of the coupling adaptor 50 to the ring assembly 22 on the tail end connector 1c. Thus, an interlocked rotation transmission mechanism is constituted by the drive pin 64 and the transmission pin 29.

On the other hand, a C-ring 65 is fitted on a proximal end portion of the rear rotary member 56, the C-ring 65 being engageable with an annular groove 32a around the inner periphery of a larger-diameter coupling portion, which is provided at the outer or front end of the rotational shaft 32, for retaining the adaptor 50 securely in the connected position relative to the probe control unit 2, precluding the possibilities of its dislocations. Further, the distal end portion of the rear rotary member 56, on the proximal side of the C-ring, is formed in a spline profile for engagement in the inner periphery 32b of an outer end portion of the rotational shaft 32 which is formed in a corresponding spline profile. Indicated at 67 is a connector member which is fixedly provided within the rear rotary member 56. This connector member 67 is constituted by an outer tubular cover 68 and an electrode rod 69, each formed of a conducting material. An insulating ring 70 is interposed between the outer cover 68 and the electrode rod 69 which are connected to the first and second tubular electrodes 61 and 63 through wires 71 and 72, respectively. Both of the outer cover 68 and electrode rod 69 are in the form of an axially split tubular structure. The rotary and stationary members may be assembled together through a bearing. In this particular embodiment, the housing 51 and the rear rotary member 56 are retained in small gap relation with each other. In case the rear rotary member 56 is loosely fitted in the housing 51 in this manner, the connector member 67 can be easily and snugly fitted in the rotational shaft 32 as the housing 51 is brought into engagement with the connection housing 47 on the part of the probe control unit 2.

With the probe coupling adaptor of the construction as described above, for the purpose of transmitting ultrasound signals of lower frequency and higher power, the ultrasound probe 1 can employ an ultrasound transducer element 13 of a large size having a broader active surface area within the end cap 10 of on the ultrasound scanner assembly which is much larger than the inside diameter of the biopsy channel 6 of the endoscope 5. The use of an ultrasound probe of this sort makes it possible to transmit ultrasound signals of higher energy levels into a body under examination and to improve the S/N ratio thanks to improvements in reception sensitivity to return echo signals.

In this case, the ultrasound probe 1 is placed in the endoscopic biopsy channel 6 from the opposite direction through an exit opening of the biopsy channel at the distal end of the endoscopic insertion instrument 5b and from the tail end connector 1c and the flexible cord 1b which are thinner than the inside diameter of the endoscopic biopsy channel 6 as described hereinbefore. More particularly, in a preparatory stage prior to introduction of the endoscopic insertion instrument 5b into a body cavity, the ultrasound probe 1 is placed in the biopsy channel 6 through an exit opening at the distal end of the endoscopic insertion instrument until the tail end connector 1c comes out of the biopsy channel 6 through the entrance housing 6a on the head grip 5a of the endoscope 5. In this instance, the tail end connector 1c is coupled with the ultrasound probe control unit 2 not directly but through the coupling adaptor 50, so that, in the first place, the tail end connector 1c which has come out through the entrance housing 6a of the endoscopic biopsy channel 6 is connected to the coupling adaptor 50. The connection to the adaptor 50 can be completed simply by fitting the electrode pin 28 in the axial hole 52a of the retainer shell 52. By so doing, the electrode pin 28 is inserted into the second tubular electrode 63 of the socket 58 on the side of the coupling adaptor 50, and at the same time the rotation transmission pin 29 is brought into engagement with the drive pin 64 on the part of the coupling adaptor 50. Simultaneously, the stopper screws 53 are urged into engagement with axial grooves on the outer periphery of the retainer shell 21. As a consequence, when the rotary members of the coupling adaptor 50 are put in rotation, the rotation transmission pin 29 is rotated with the drive pin 64 while the retainer shell 21 of the ultrasound probe 1 is blocked against rotational movements by engagement with the retainer cap 52 of the adaptor 50.

Thus, the ultrasound probe can be connected to the coupling adaptor 50 quite easily by gripping in one hand the adaptor 50 which is in a free state, without possibilities of exerting strong distorting forces on the thin tail end connector 1c. Besides, the relatively thin and fragile tail end connector 1c, which is completely surrounded by the coupling adaptor 50 of high strength, can be protected against damages which might result from coupling and uncoupling operations. For precluding the possibilities of colliding contact with nearby objects, it is preferable that the entrance housing 6a of the biopsy channel be connected to the coupling adaptor 60 as soon as it is led out through the entrance housing 6a of the biopsy channel. The coupling adaptor 50 itself may be immediately connected to the probe control unit 2 if desired, but it may be left in a free or unplugged state in case it could impose restrictions on operations of the endoscope 5.

Figure 8:
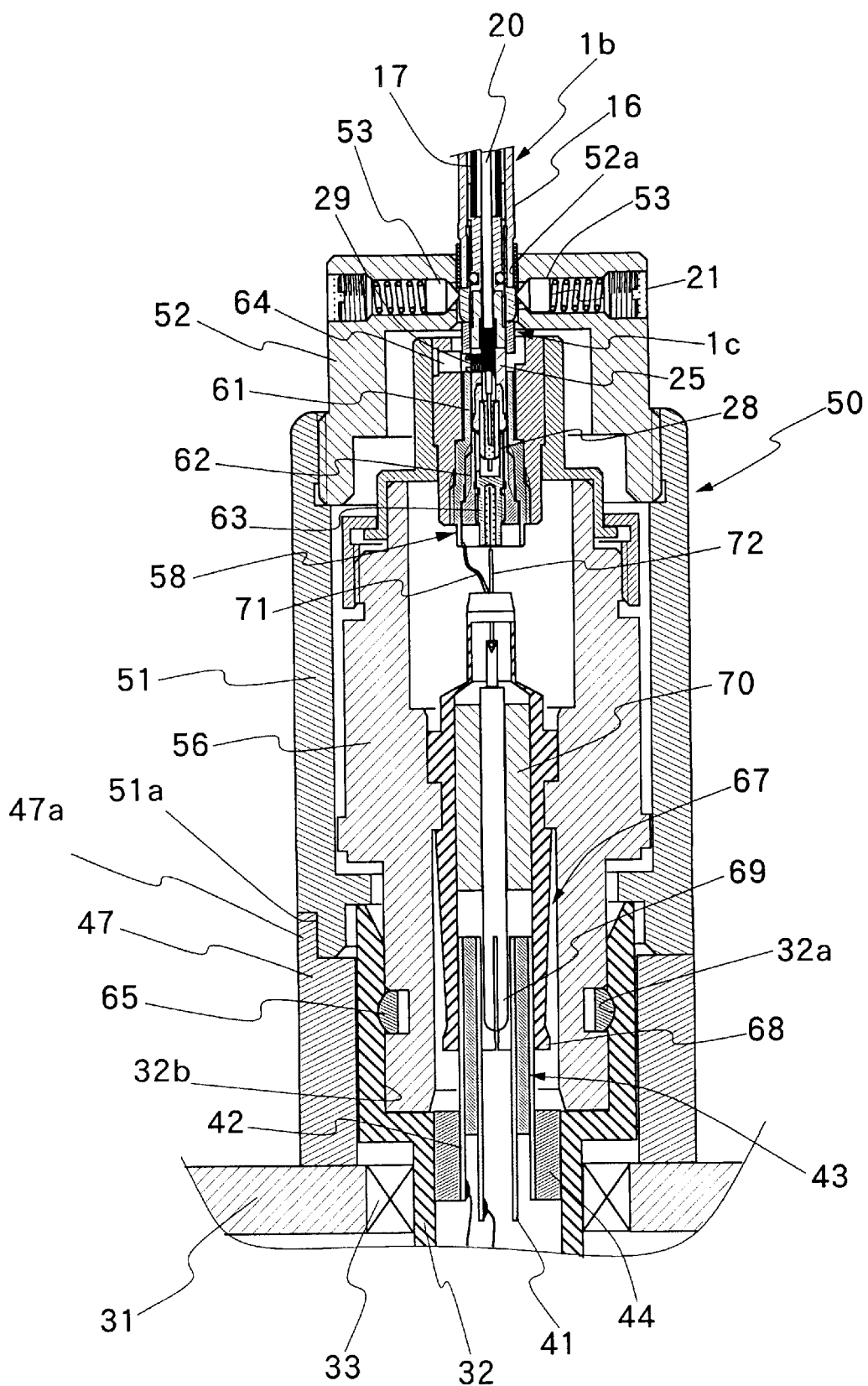
FIG. 8 is a fragmentary sectional view of the ultrasound probe which is coupled with the probe control unit through the coupling adaptor.

At the time of an ultrasound examination, the coupling adaptor 50 is connected to the probe control unit 2 as shown in FIG. 8. Although the probe control unit 2 is mounted on the movable support arm 8, the coupling mechanism could be subjected to various external forces from various directions. However, when connecting the ultrasound probe 1 to the probe control unit 2, the coupling adaptor 50 functions to protect the tail end connector 1c, which is the most fragile part of the coupling mechanism, because it is the adaptor 50 itself that has to be directly connected to the probe control unit 2. Upon coupling the rear rotary member 56 and housing 51 of the adaptor 50 with the rotational shaft 32 and connection housing 47 on the casing 31 of the probe control unit 2 respectively, the connector member 67 is connected with the electrode member 40 on the part of the probe control unit 2. As a consequence, rotation of the rotational shaft 32 is transmitted to the ring assembly 22 of the ultrasound probe 1 through the rear and front rotary members 56 and 57 of the adaptor 50, and further to the flexible shaft 17 which is coupled with the ring assembly 22. The signal lines 20a and 20b of the coaxial cable 20, from the ultrasound transducer element 13, are electrically connected to the first and second tubular electrodes 61 and 63 of the socket 58 on the coupling adaptor 50 through the electrode pin 28 and transmission pin 29, to the inner and outer sleeves 41 and 42 of the electrode member 40 on the part of the probe control unit 2 through the wires 71 and 72, and to the ultrasound image observation terminal 3 through the rotary connector 45 and cable 9, respectively.

Accordingly, upon starting the electric motor 36, its rotation is transmitted through the flexible shaft 17 to the rotary member 14 at the distal end of the ultrasound probe 1 to rotate the ultrasound transducer element 13 which is mounted on the rotary member 14. Simultaneously, on the basis of angular position signals from the encoder 38, drive pules are applied to the ultrasound transducer element 13 to transmit ultrasound pulses at predetermined angular intervals, while receiving return echoes. The received return echo signals are transferred to the ultrasound image observation terminal 3 and processed to generate ultrasound images for display on the monitor screen 4.

In the above-described embodiment, the rotation of the rotational shaft 32 is transmitted indirectly to the ultrasound probe 1 through the coupling adaptor 50 which electrically and rotationally couples the ultrasound probe 1 with the probe control unit 2. In order to transmit the rotation accurately in a stabilized state, it is necessary to maintain the rotational axes of rotary members of the coupling adaptor 50 and the ring assembly 22 of the tail end connector 1c at the proximal end of the ultrasound probe 1 in alignment with the axis of the rotational shaft 32 on the probe control unit 2. In this regard, the tail end connector 1c is allowed to move to some extent in radial directions to absorb deviations of its rotational axis since it is maintained substantially in a floating state by resilient actions of the springs 55 of the fixing screws 53. However, it becomes difficult to transmit rotation smoothly and stably to the ultrasound transducer element 13 when the rotational axes are misaligned and deviated beyond the floating range due to irregular rotational motions caused by eccentric or radial drifting of the rotational axes, in addition to concentration of stresses on the ring assembly 22 of the tail end connector 1c which is the most fragile part throughout the rotational coupling mechanism.

Figure 9:
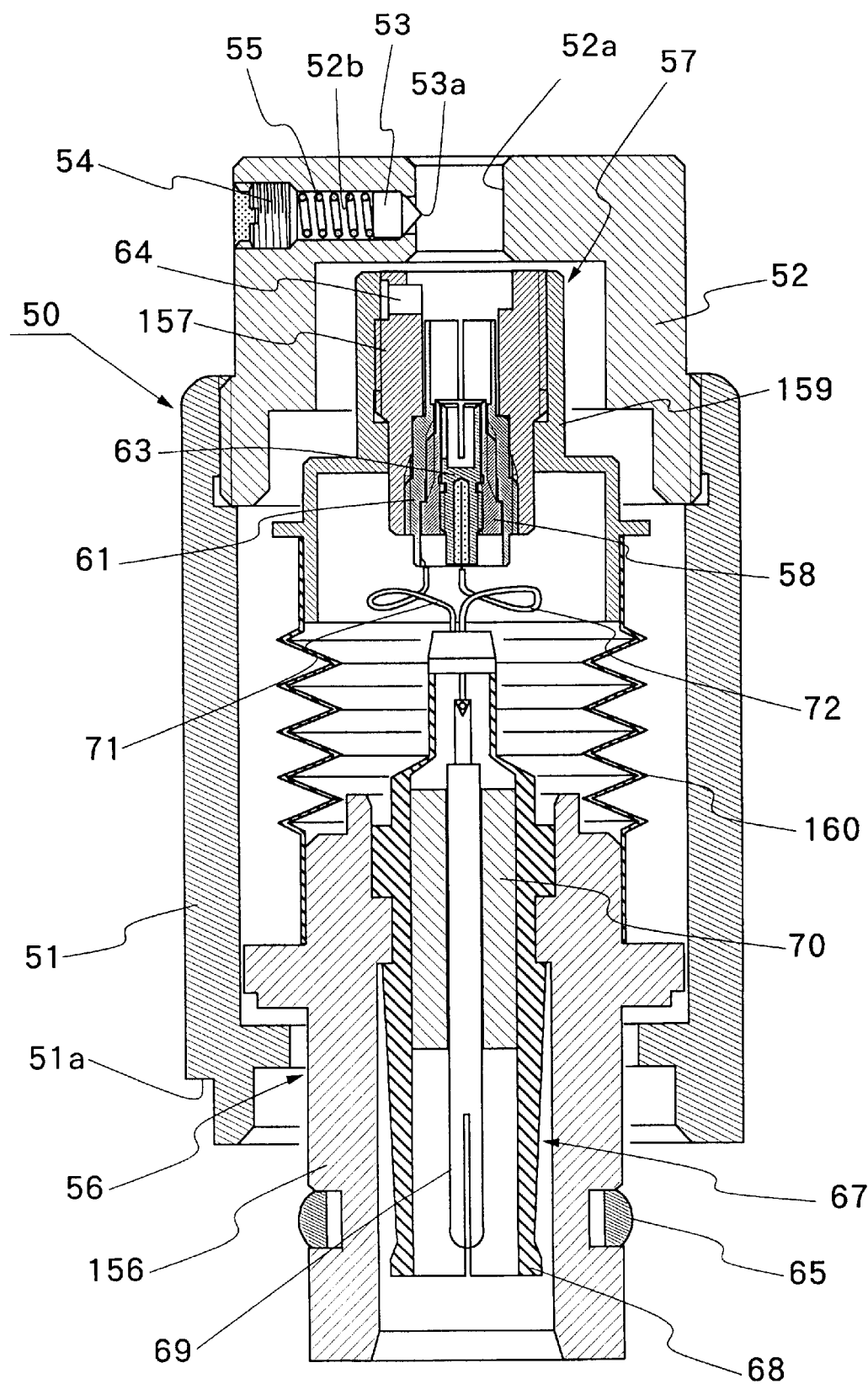
FIG. 9 is a schematic sectional view of a coupling adaptor in a second embodiment of the present invention.

In order to ensure smooth transmission of rotation despite deviations of rotational axes in the coupling mechanism, it is preferable to employ the arrangements as shown in FIG. 9. In the following description on the embodiment of FIG. 9, those component parts which are identical or equivalent with the counterparts in the foregoing first embodiment are simply designated by similar reference numerals or characters to avoid repetition of same explanations.

In this instance, the rotary members of the coupling adaptor 50 include a front rotary member 157 of a hollow cylindrical shape fitted with a socket 58 to be detachably coupled with the tail end connector 1c of the ultrasound probe 1, and a larger rear rotary member 156 similarly of a hollow cylindrical shape fitted with a connector member 67 to be detachably coupled with the rotational shaft 32 on the probe control unit 2. The front and rear rotary members 157 and 156 are connected with each other not rigidly but through a flexible rotation transmission means which can absorb relative deviations of rotational axes of the two rotary members. More specifically, in this particular embodiment, the front and rear rotary members 157 and 156 are connected with each other through a bellow member 160 which is fixedly fitted on a fore small-diameter portion of the rear rotary member 156 and a retainer ring 159 of the front rotary member 157. The bellows 160 function to transmit rotation of the rear rotary member 156 securely to the front rotary member 157 and at the same time to absorb positional deviations between the rotational axes of the two rotary members.

With the arrangements just described, the rear rotary member 156 which is coupled with the rotational shaft 32 of the probe control unit 2 is allowed to adapt itself into alignment with the rotational shaft 32 of the latter. On the other hand, deviations of the rotational axis of the tail end connector 1c of the ultrasound probe 1, which is coupled with the socket 58 of the adaptor, are absorbed by flexural movements of the bellows 160 even if the deviations exceed the range of adaptive floating movements allowed by the fixing screws 53. Consequently, there is no possibility of irregular rotational motions or eccentric drifting of the rotational axis on the side of the tail end connector 1c of the ultrasound probe 1 while rotation is transmitted from the rotational shaft 32 to the tail end connector 1c of the probe 1 through the coupling adaptor 50 during an ultrasound scan operation, thus precluding the damages which would otherwise result from concentration of stresses on fragile parts of the tail end connector 1c.

Figure 10:
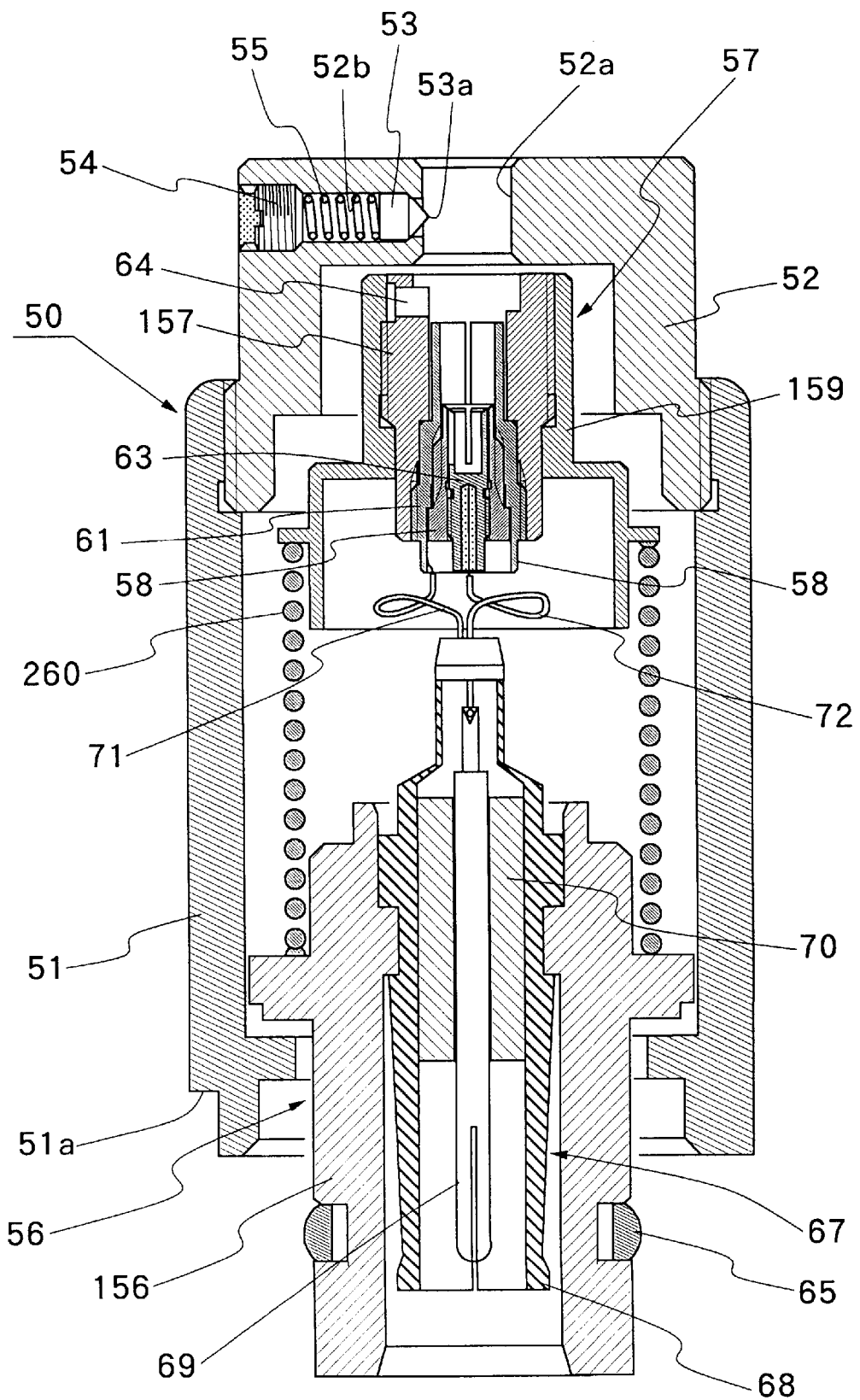
FIG. 10 is a schematic sectional view of a coupling adaptor in a third embodiment of the present invention.

Instead of using the above-described bellow member 160, the flexible rotation transmission means may employ a flexible coil tube 260 as shown in FIG. 10. In case the flexible transmission member is constituted by a resilient coil tube 260, it is necessary to prevent disturbances in coil pitch which occur when the flexible coil is flexed in directions perpendicular to the rotational axis during transmission of rotation. To this end, for example, the flexible coil tube may be constituted by a tube of a tightly wound coil.

Figure 11:
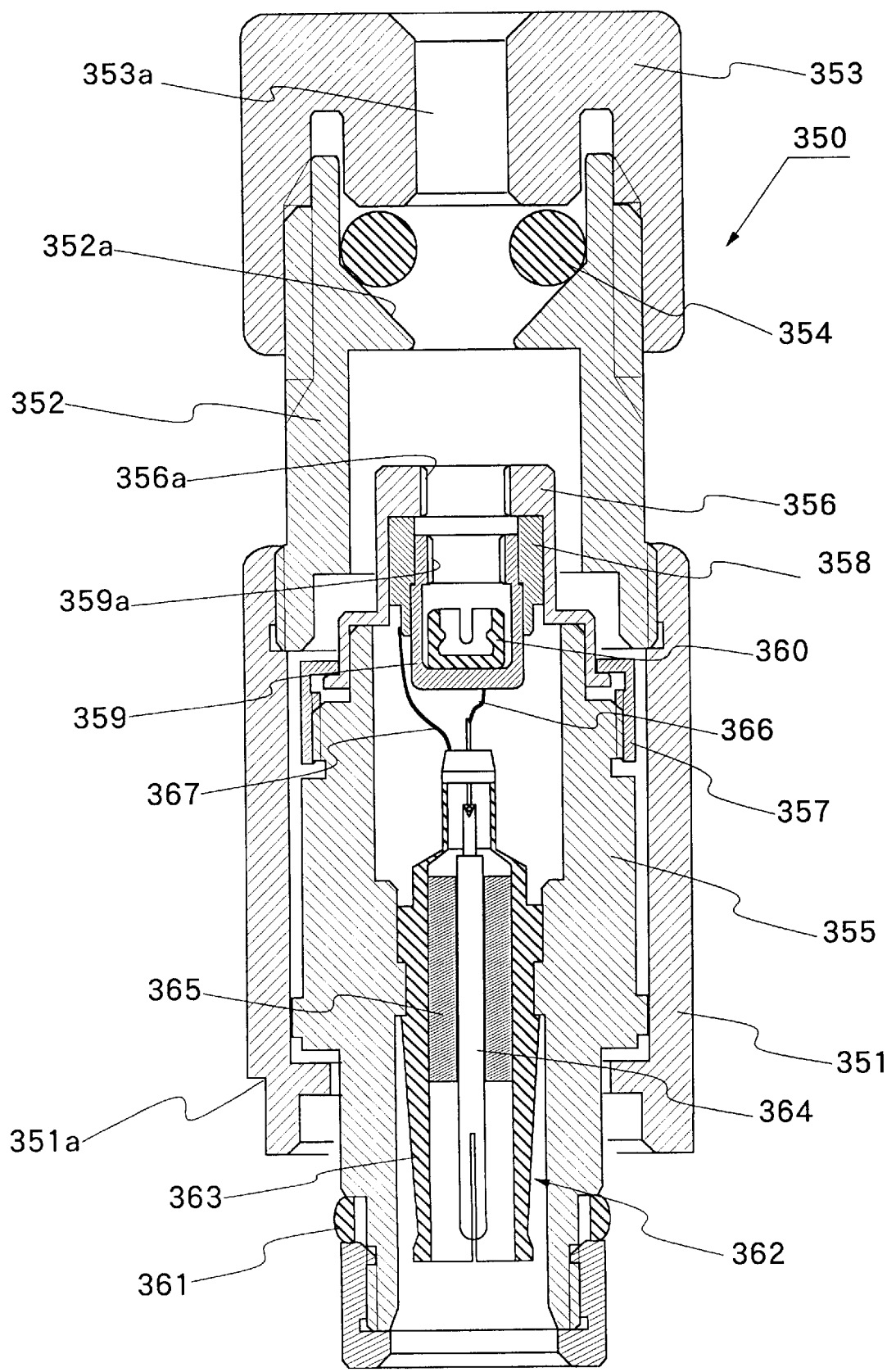
FIG. 11 is another schematic sectional view of the coupling adaptor of the third embodiment in an applied position.

Illustrated in FIG. 11 is another modification of the coupling adaptor according to the present invention. In that figure, indicated at 350 is the coupling adaptor itself having, as a stationary member, a housing 351 which is formed substantially in a cylindrical shape and which is detachably connectible to the connecting housing 47 of the probe control unit 2. A retainer shell 352 is threaded into a fore end portion of the connecting housing 351. A stopper nut 353 is threaded on the outer periphery of the retainer shell 352, which is provided with a tapered or inwardly converging guide surface 352a on the inner peripheral side thereof. A rotation blocking resilient brake ring 354 is fitted in the inner periphery of the retainer shell 352 in engagement with the tapered guide surface 352a. As the stopper nut 353 is threaded on the retainer shell progressively to a greater degree, the resilient ring 354 is thereby pushed in along the tapered guide surface 352a and shrunk into a smaller diameter. The stopper nut 353 is provided with an axial through hole 353a as a guide passage for the tail end connector 1c and flexible cord 1b of the ultrasound probe 1. In a free state, the resilient brake ring 354 has an inside diameter which is larger than the outside diameters of the tail end connector 1c and flexible cord 1b.

As rotary members, the coupling adaptor 350 is provided with a rear rotary member 355 of a larger diameter and a front rotary member 356 of a smaller diameter, which are connected with each other through a box nut 357. The rear rotary member 355 is detachably coupled with the probe control unit 2, while the front rotary member 356 is detachably coupled with the tail end connector 1c of the ultrasound probe 1. The front rotary member 356 is provided with an axial passage 356a with a spline profile to receive and block relative rotational movements of the tail end connector 1c of the ultrasound probe 1 which is formed in a corresponding spline profile. An insulator ring 358 is fixedly fitted in the inner periphery of the front rotary member 356, and in turn a socket 359 is fixedly fitted in the insulator ring 358. The socket 359 is in the form of a hollow cylinder which is closed at one end, and provided with spline teeth 359a on the inner periphery. A retainer member 360 is securely fixed on the bottom of the socket member 359. On the other hand, a connector member 362 is fixedly provided within the rear rotary member 355. The connector member 362 includes an outer tube 363 and an electrode rod 364, which are both formed of a conducting material, and an insulator ring 365 which is interposed between the outer tube 363 and electrode rod 364. The outer tube 363 is connected with the front rotary member 356 through a wire 366, while the socket 359 is connected with the electrode rod 364 through a wire 367.

Figure 12:
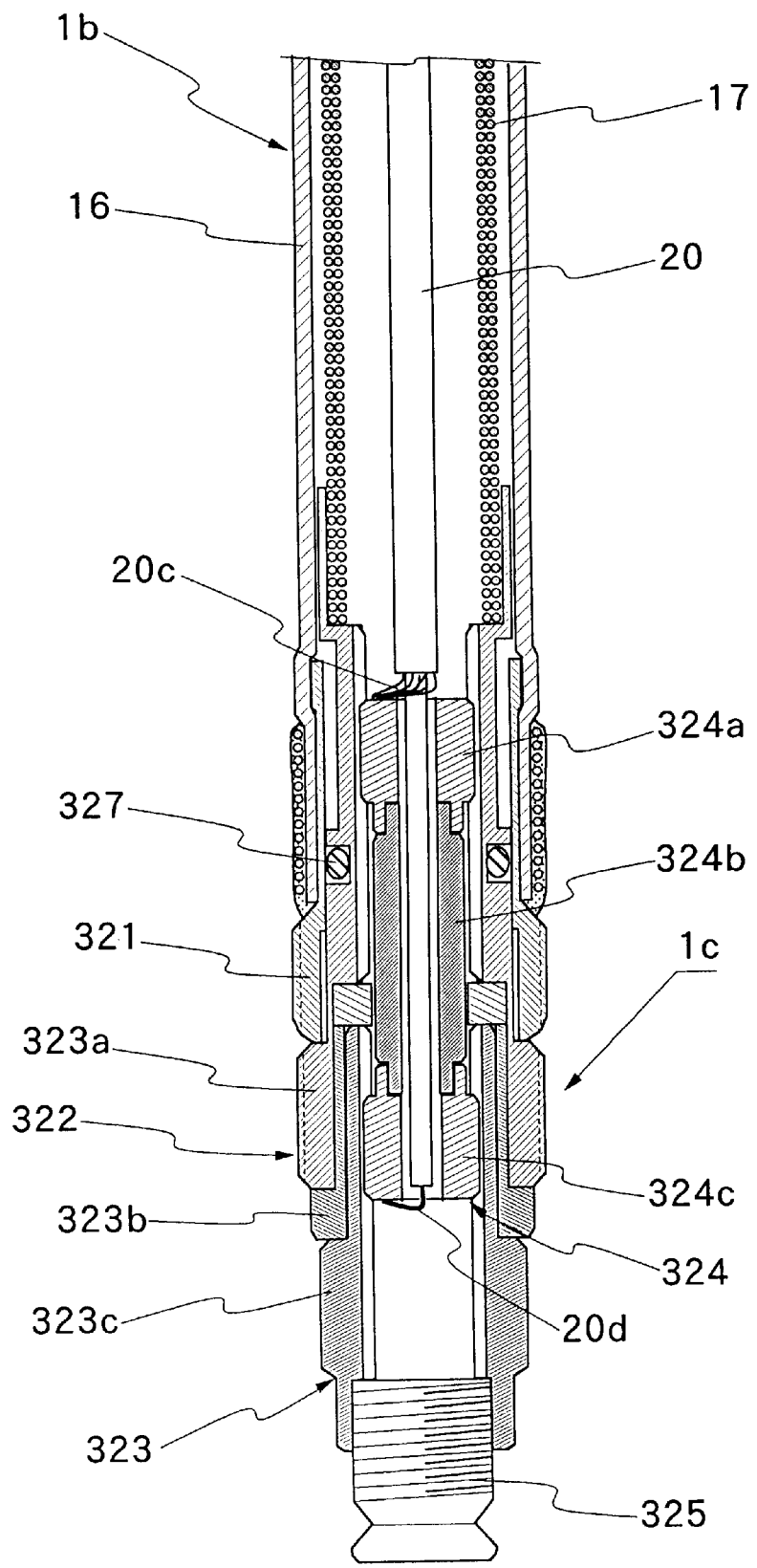
FIG. 12 is a longitudinal sectional view of an ultrasound probe with a tail end connector fitted in the coupling adaptor of FIG. 11.

For use with the coupling adaptor 350, preferably the tail end connector 1c of the ultrasound probe 1 is arranged as illustrated in FIG. 12. More specifically, in this instance, the tail end connector 1c includes a rigid pipe 321 which is securely connected to the proximal end of the flexible tube 16, and a rotational coupler 322 which is connected to the proximal end of the flexible transmission shaft 17. The rotational coupler 322 is constituted by a ring assembly 323, a contact member 324 and a coupling piece 325. The ring assembly 323 is composed of three rings, including a first ring member 323a which is largest in axial length and securely fixed at one end thereof to the flexible transmission shaft 17. The first ring member 323a is slidably fitted in the rigid pipe 321, which is on the stationary side of the connector 1c, through an interposed seal member 327. Further, the first ring member 323a is extended toward the proximal end by a predetermined length on the proximal side of the rigid pipe 321. Second and third ring members 323b and 323c are successively fitted in and connected to the first ring member 323a on the proximal side thereof. The first and third ring members 323a and 323c are formed of a conducting material to serve as electrodes, while the second ring member 323b is formed of an insulating material to function as an insulator ring.

On the other hand, the contact member 324 includes a first contact portion 324a, an insulating portion 324b and a second contact portion 324c which are successively connected one after another in the axial direction. The first contact portion 324a is fitted in the first ring member 323a of the ring assembly 323, while the second contact portion 324c is fitted in the third ring member 323c. The proximal end of the coaxial cable 20, which is provided coextensively within the flexible cord 1b, is connected to the contact member 324. More specifically, the shield wire 20c and core wire 20d of the coaxial cable 20 are electrically connected to the first and second contact portions 324a and 324c, respectively. These first and second contact portions 324a and 324c are splined with the first and third ring members 323a and 323c of the ring assembly 323, respectively. Accordingly, the contact member 324 is movable in the axial direction relative to the ring assembly 323, but locked with the latter in the rotational direction. Irrespective of the position of the axially slidable contact member 324, the shield wire 20c and core wire 20d are electrically connected with the first and ring members 323a and 323c through the first and second contact portions 324a and 324c of the contact member 324, respectively.

Figure 13:
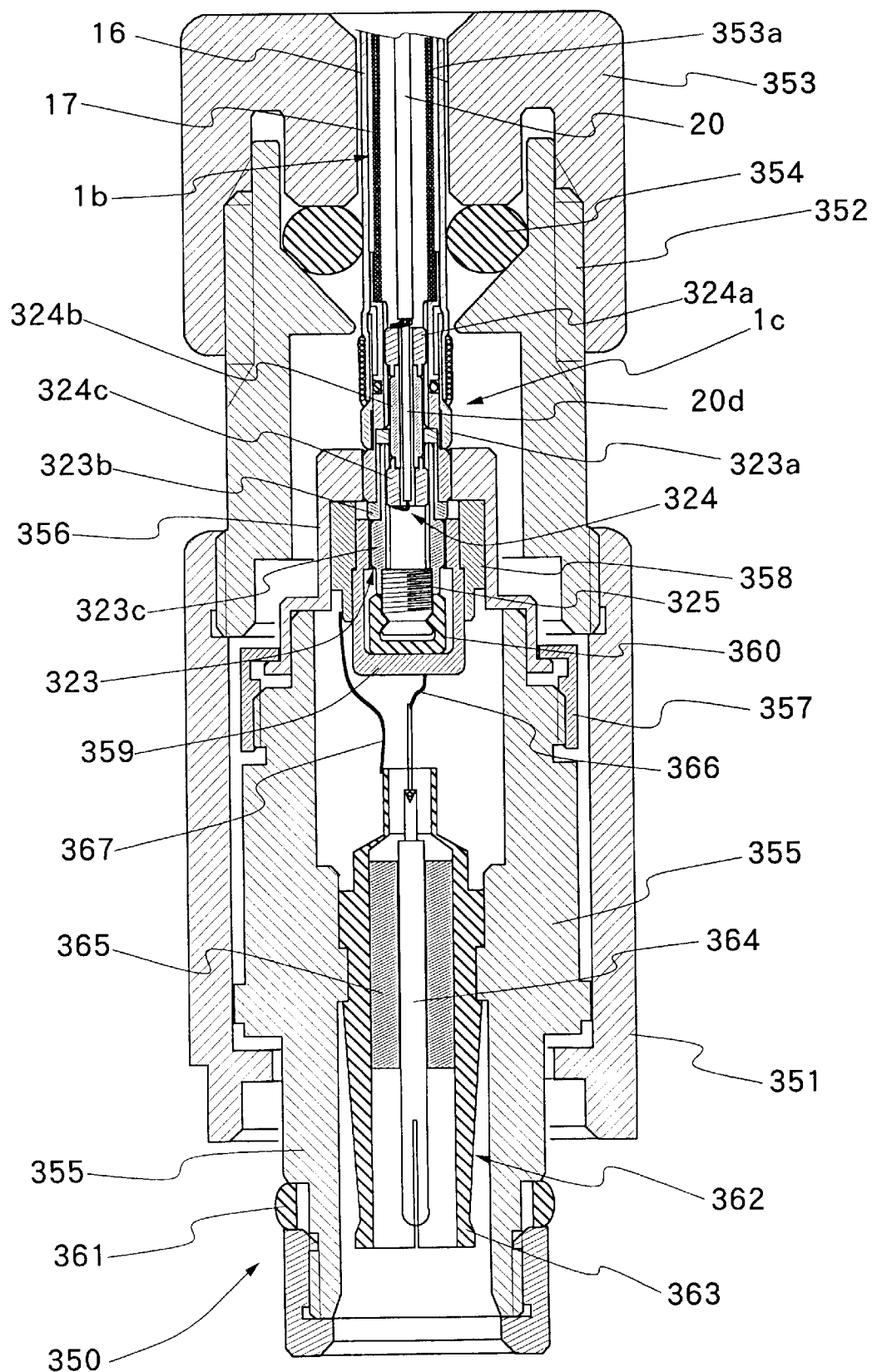
FIG. 13 is a longitudinal sectional view of the ultrasound probe of FIG. 12, having its tail end connector fitted in the coupling adaptor of FIG. 11.

The tail end connector 1c of the ultrasound probe 1, with the above-described construction, is coupled with an adaptor 350 in the manner as shown in FIG. 13. In the coupled state shown, the first ring member 323a of the ring assembly 323 of the tail end connector 1c is splined with the axial passage 356a of the front rotary member 356, and the coupling piece 325 at the distal end of the tail end connector 1c is snapped in the retainer member 360. In this coupled state, the stopper nut 354 is threaded further onto the retainer shell 352, whereupon the resilient rotation-blocking ring 354 is shrunk into a smaller diameter as it is pushed in along the tapered guide surface 352a and finally pressed against the outer periphery of the flexible cord 1b of the ultrasound probe 1 to arrest the flexible cord 1b against rotational movements.

With the tail end connector 1c of the construction as described above, the pulling forces, which may act on the coaxial cable 20 as the flexible cord 1b is flexed along a bent path of insertion, can be absorbed by axial displacements of the contact member 324 within the rotational ring assembly 323 although the range of its axial displacements is limited. Therefore, in use, the coaxial cable 20 is always kept from abnormally strong pulling and compressing forces to preclude wire breakage, disjoining of connected parts or similar troubles.

The proximal end of the flexible transmission shaft 17, which is constituted by tightly wound metal wires, is securely connected to the rotary ring 23 which is made of a metallic material. Upon turning on the ultrasound image observation terminal 3, the power source is connected to the rotary ring 23 which constitutes part of current supply paths of the probe. As seen particularly in FIGS. 3 and 4, the fore distal end of the flexible transmission shaft 17 is securely connected to the hollow neck member 18 in face to face relation with the connecting member 11. In case the connecting member 11 is formed of a metallic material, it becomes necessary to prevent electric current from flowing into the patient's body from the rotary ring 23 through the flexible shaft 17 and the connecting member 11. In order to prevent troubles of this sort, a front end portion of the flexible transmission shaft 17 which is connected to the ultrasound scanner assembly 1a should be electrically insulated from its proximal end portion which is connected to the tail end connector 1c, for example, in the manner as shown in FIG. 14.

Figure 14:
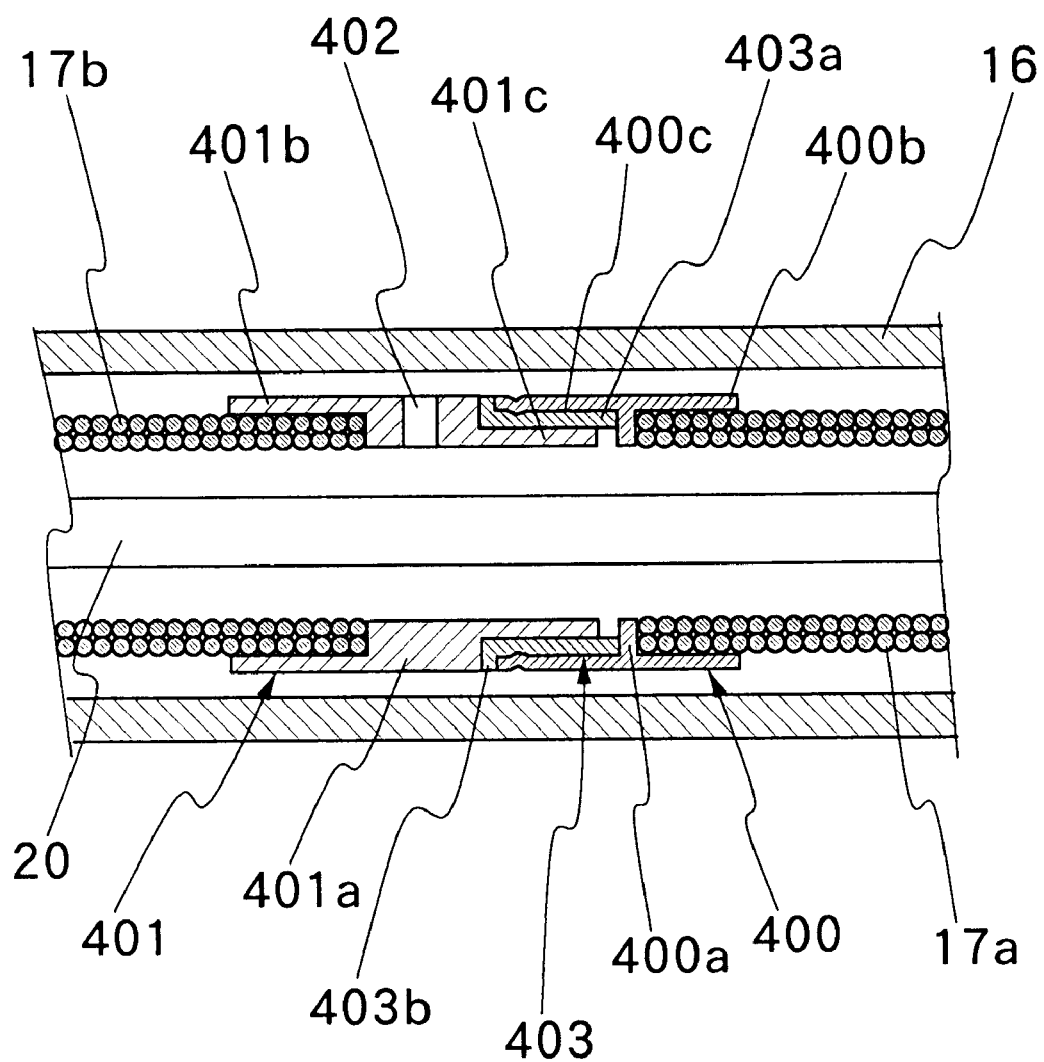
FIG. 14 is a fragmentary sectional view of a joint portion of a flexible rotation transmission shaft consisting of a number of flexible shaft sections.

More specifically, in the case of the embodiment shown in FIG. 14, the flexible transmission shaft 17 within the flexible cord 1b is divided into two sections, namely, into a front section 17a on the side of the ultrasound scanner assembly 1a and a rear section 17b on the side of the tail end connector 1c. These front and rear sections 17a and 17b of the flexible transmission shaft 17 have metallic joint rings 400 and 401 securely fixed to the respective meeting ends. The joint ring 400 which is fixed on the proximal end of the front section 17a has, on the front and rear sides of its annular main body 400a, an annular front extension 400b which is securely fitted on the front section 17a of the flexible shaft 17 and an annular rear extension 400c. The joint ring 401 which is fixed on the fore end of the rear section 17b of the flexible shaft 17 has, on the opposite sides of its annular main body 401a, an annular rear extension 401b which is securely fitted on the fore end of the rear section 17b of the flexible shaft 17 and an annular front extension 401c which is fitted in the rear flange portion 400c of the joint ring 400. The rear and front extensions 401b and 401c of the joint ring 401 are thinned down on the inner and outer peripheral sides, respectively, in a diametrically staggered fashion. The annular main body 401a of the joint ring 401 is provided with one or a plural number of air escape holes 401. An insulator ring 403 of a synthetic resin material is interposed between the rear and front flange portions 400c and 401c of the joint rings 400 and 401 thereby to electrically insulate the front and rear sections 17a and 17b of the flexible shaft 17 from each other. The insulator ring 403 is provided with a radially extending spacer portion at one end of its annular body 403a which is in fitting engagement with the rear and front extensions 400c and 401c of the joint rings 400 and 401 on the outer and inner sides thereof.

Figure 15:
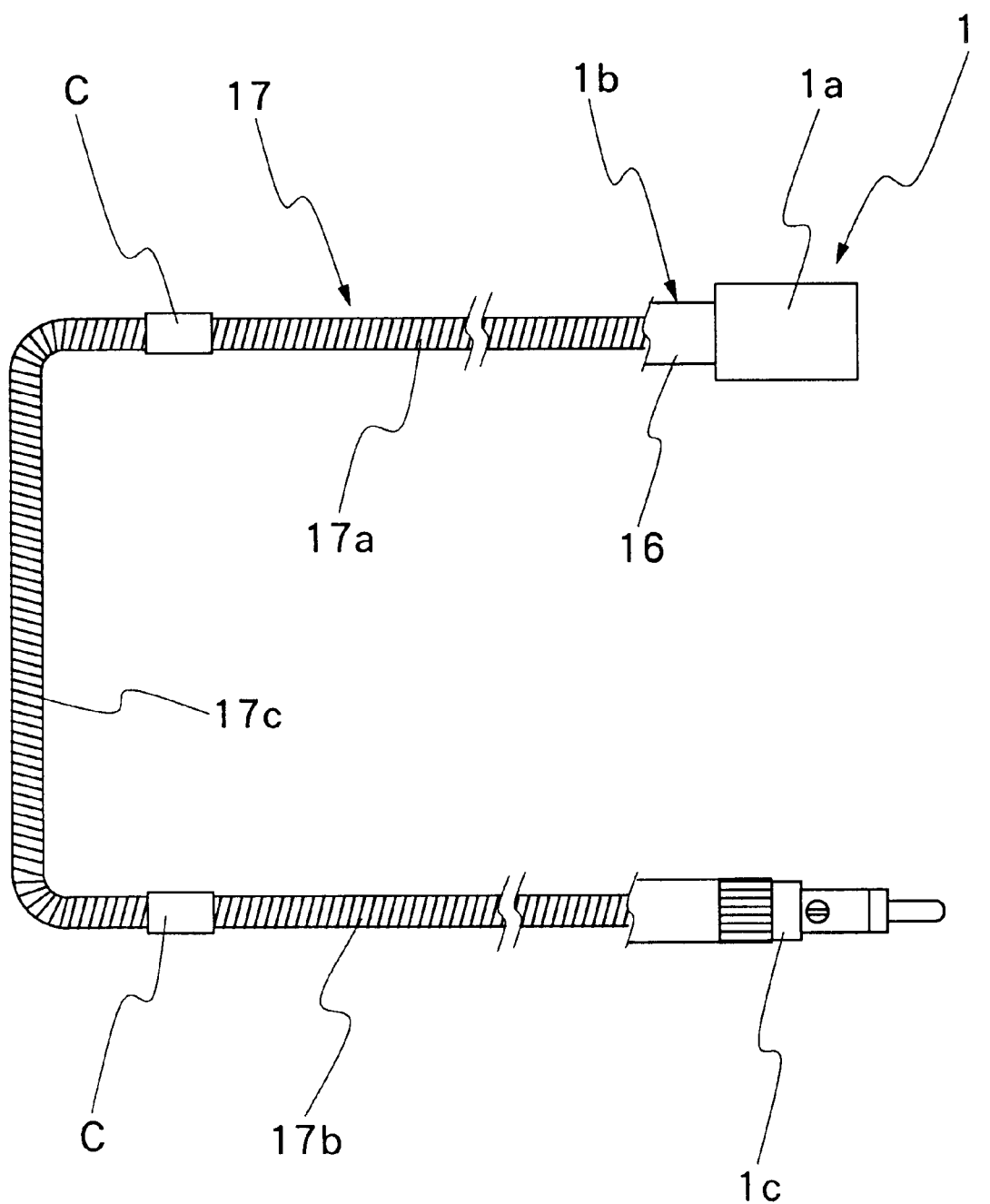
FIG. 15 is a schematic view of a flexible transmission shaft which is divided into three sections.

Besides, in case a number of divided sections of the flexible transmission shaft 17 are connected by the use of joint rings in this manner, it becomes possible to improve rotational follow-up characteristics of the front section 17a to rotations of the proximal end of the rear section 17b of the flexible transmission shaft 17, permitting to preclude lags of rotations in transmission and to prevent irregular rotational movements which are attributable to a lengthy transmission shaft. Improvements in these functions can be further augmented by dividing the flexible transmission shaft 17 into three sections, i.e., a front section 17a, a rear section 17b and an intermediate section 17c which are successively joined together by the use of similar joint rings and insulator rings as indicated at C in FIG. 15.

What is claimed is:

1. In an ultrasound examination system employing an endoscopically inserting ultrasound probe to be introduced into a body cavity through a biopsy channel provided in an endoscopic insertion instrument, said ultrasound probe having a bulky ultrasound scanner assembly at the nose end of an elongated flexible cord containing a flexible rotation transmission means and an electrical signal cable for an ultrasound transducer element on said ultrasound scanner assembly, and a thin and narrow tail end connector provided at the tail end of said flexible cord for electrically and rotationally coupling said ultrasound probe with a rotational drive and electrical wiring contacts on a separate probe control unit, both of said flexible cord and tail end connector having an outside diameter smaller than inside diameter of said endoscopic biopsy channel for passage therethrough:

a coupling adaptor to be disconnectibly connected to said tail end connector of said endoscopically inserting ultrasound probe for electrically and rotationally coupling same with said probe control unit stably in a protected state, said coupling adaptor having within a stationary housing a pair of rotationally interconnected front and rear rotary members to be disconnectibly coupled with said tail end connector and said rotational drive means on said probe control unit, respectively, said front and rear rotary members of said coupling adaptor internally carrying electrical connection means to establish electrical connections between said ultrasound probe and said probe control unit when coupled therewith to transmit rotation from said rotational drive means to said ultrasound transducer element.

2. A coupling adaptor for an endoscopically inserting ultrasound probe as defined in claim 1, wherein said flexible rotation transmission means of said ultrasound probe is in the form of a tubular flexible transmission shaft fitted in a flexible sheathing tube to transmit rotation to said ultrasound transducer element, said tubular transmission shaft internally providing a passage for said electrical cable to be connected to said ultrasound transducer element, and said tail end connector of said ultrasound probe is comprised of a stationary part connected to said flexible tube and a rotating part connected to said flexible transmission shaft and electrical cable which are passed through said stationary part, said stationary part of said tail end connector being adapted to fit in said stationary housing of said coupling adaptor in a rotationally blocked state while said rotating part is adapted to fit in said front rotary member for rotation therewith when said tail end connector of said ultrasound probe is connected with said coupling adaptor.

3. A coupling adaptor for an endoscopically inserting ultrasound probe as defined in claim 2, wherein said rotating part of said tail end connector of said ultrasound prove is provided with a transmission pin to be rotationally interlocked with a drive pin provided on said front rotary member of said coupling adaptor when said tail end connector of said ultrasound probe is fully inserted into said front rotary member of said coupling adaptor.

4. A coupling adaptor for an endoscopically inserting ultrasound probe as defined in claim 3, wherein said front and rear rotary members are connected with each other through a flexible rotation transmission member.

5. A coupling adaptor for an endoscopically inserting ultrasound probe as defined in claim 4, wherein a pair of electrodes are provided on each one of said front and rear rotary members of said coupling adaptor, an electrode on said front rotary member being connected with a corresponding electrode on said rear rotary member through a flexible cable.

6. A coupling adaptor for an endoscopically inserting ultrasound probe as defined in claim 4, wherein said flexible rotation transmission member is constituted by a coil tube or bellows.

7. A coupling adaptor for an endoscopically inserting ultrasound probe as defined in claim 5, wherein said coupling adaptor further comprises a floating anti-rotation mechanism adapted to block rotational movements of said stationary part of said tail end connector while permitting a certain degree of eccentric radial movements of the latter.

8. A coupling adaptor for an endoscopically inserting ultrasound probe as defined in claim 2, wherein said rotation transmission means of said ultrasound probe is constituted by a flexible shaft of tightly wound coils sheathed in a flexible tube, and said rotating part of said tail end connector comprises a ring assembly connected to said flexible transmission shaft and a contact member fitted in said ring assembly non-rotatably but slidably over a predetermined distance in the axial direction, said contact member having a pair of contact bodies axially separated from each other by an interposed insulating member and connected to wires from said electrical cable, and said ring assembly including a pair of electrode portions in sliding engagement with said contact bodies of said contact member and an insulating ring interposed between said electrode portions.

9. A coupling adaptor for an endoscopically inserting ultrasound probe as defined in claim 8, wherein said contact bodies of said contact member are splined with said electrode portions of said ring assembly.

10. A coupling adaptor for an endoscopically inserting ultrasound probe as defined in claim 2, wherein said rotation transmission member of said ultrasound probe is constituted b a flexible shaft of tightly wound metal wire coils, said flexible shaft being divided at least into a front section connected from said ultrasound scanner assembly and a rear section connected from said tail end connector of said ultrasound probe, said front and rear sections being rotationally joined with each other through an electrically insulating member.

11. A coupling adaptor for an endoscopically inserting ultrasound probe as defined in claim 10, wherein said front and rear sections of said flexible shaft are rotationally joined with each other at an axially intermediate portion of said flexible cord through joint means and an interposed electrically insulating member.

12. A coupling adaptor for an endoscopically inserting ultrasound probe as defined in claim 10, further comprising at least an intermediate section connected between and rotationally joined with said front and rear sections of said flexible shaft through joint means containing an electrically insulating member at least at in a joint portion with either said front or rear section of said flexible shaft.

13. A coupling adaptor for an endoscopically inserting ultrasound probe as defined in claim 10, wherein said divided sections of said flexible shaft are rotationally jointed with each other through a couple of metallic joint rings securely fitted one on the other through an insulator ring interposed between said metallic joint rings.

14. A coupling adaptor for an endoscopically inserting ultrasound probe as defined in claim 13, wherein said insulator ring is comprised of an annular body portion having a predetermined axial length, and a radially projecting spacer portion provided at one axial end of said annular body portion, said spacer portion being abutted by opposing ends of said metallic joint rings to hold same in predetermined spaced positions from each other when fitted on the inner and outer sides of said annular body portion.

15. A coupling adaptor for an endoscopically inserting ultrasound probe as defined in claim 13, wherein one of said metallic joint rings is provided with a radial air escape hole in an annular body portion out of fitting engagement with said insulator ring.

* * * * *